United States Patent [19]
Simonelli et al.

[11] Patent Number: 5,913,246
[45] Date of Patent: Jun. 15, 1999

[54] MECHANICAL STRESS TEST MACHINE

[76] Inventors: Robert Joseph Simonelli, #2 Bunker Hill Rd., Shrewsbury, Mass. 01545; Robert James Simonelli, 107 Orton St. Extension, Worcester, Mass. 01604; James M. Simonelli, 98 Fitzpatrick Rd., Grafton, Mass. 01519

[21] Appl. No.: 08/968,600

[22] Filed: Nov. 13, 1997

Related U.S. Application Data

[60] Provisional application No. 60/031,146, Nov. 19, 1996.

[51] Int. Cl.[6] ........................................... G01N 3/32
[52] U.S. Cl. ................................. 73/808; 73/806; 73/794; 73/856
[58] Field of Search ............................... 73/788, 808, 794, 73/806, 818, 819, 826, 831, 846, 853, 856

[56] References Cited

U.S. PATENT DOCUMENTS

| | | | |
|---|---|---|---|
| 3,733,895 | 5/1973 | Ishida | 73/161 |
| 3,808,885 | 5/1974 | Carlson | 73/161 |
| 4,198,870 | 4/1980 | Barker et al. | 73/799 |
| 4,374,474 | 2/1983 | Cain | 73/433 |
| 5,340,951 | 8/1994 | Hungerbuhler et al. | 73/862.621 |
| 5,421,205 | 6/1995 | Pohl | 73/833 |

*Primary Examiner*—Max H. Noori

[57] ABSTRACT

The invention is a machine for the cyclic load testing in tension, compression, torsion, shear, or any combination thereof of any one of a number of different sizes, types and configurations of test specimens at a fixed or adjustable predetermined load and cycle rate and comprising a machine frame in which is mounted a drive shaft, any number of intermediate shafts as required, and a camshaft or crankshaft. At the workstation of the machine, appropriate fixtures and tooling are either fixed, rotating, or in motion, as required to conduct the particular test to be performed. When the test specimen is to be in motion, the motion may be derived from a driving source separate from the primary mover or camshaft, for instance but not limited to an independent motor or cylinder. This source of motion may also be taken through a drive train or any suitable means from the same driving source as the camshaft or from the camshaft itself or from any other moving member in the system. A motion is ultimately imparted to drive the test specimen holder, thereby setting the test specimen in motion.

20 Claims, 10 Drawing Sheets

RIGHT SIDE VIEW D-D

PARTIAL SECTION B-B

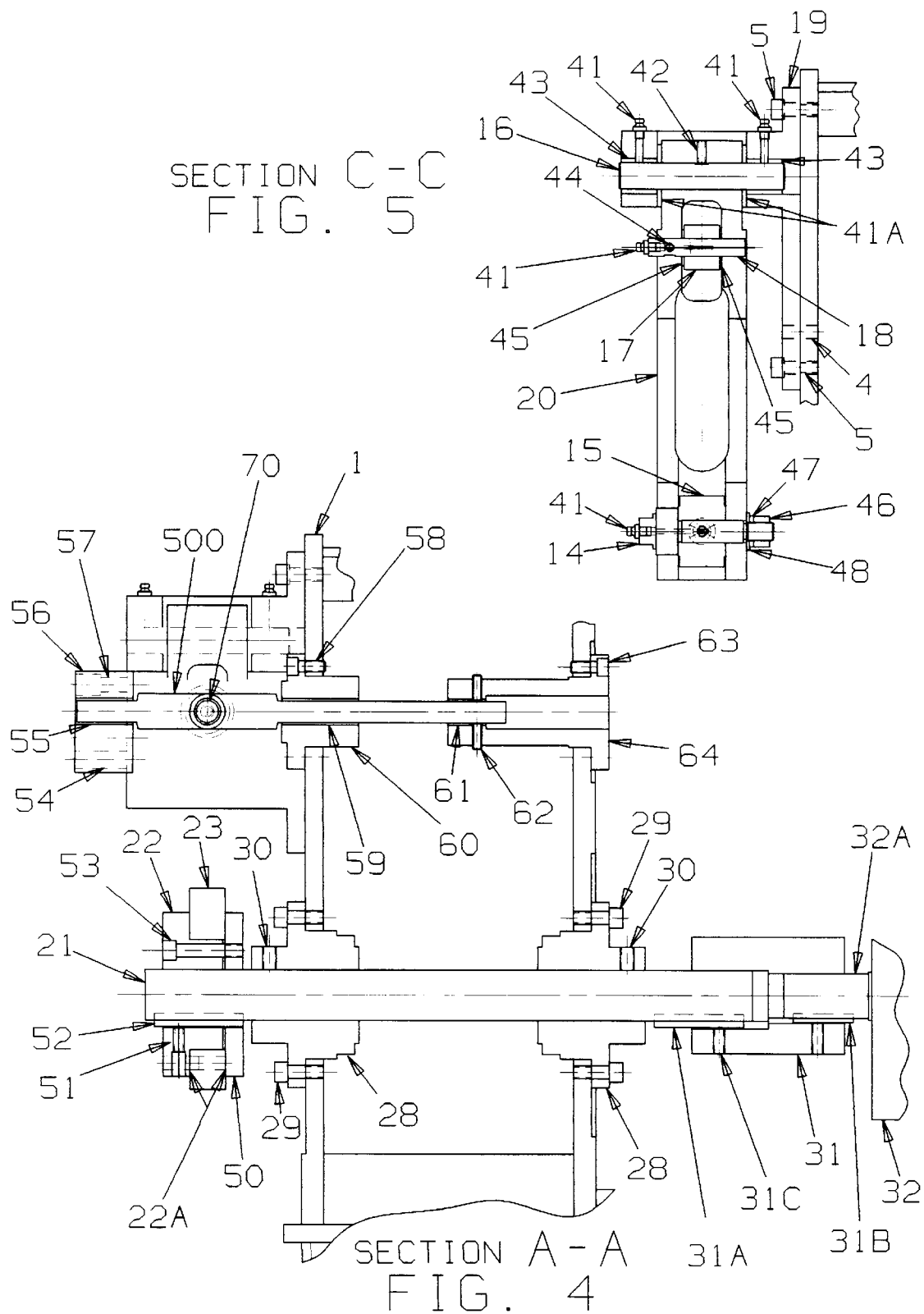

SECTION E-E

SECTION F-F

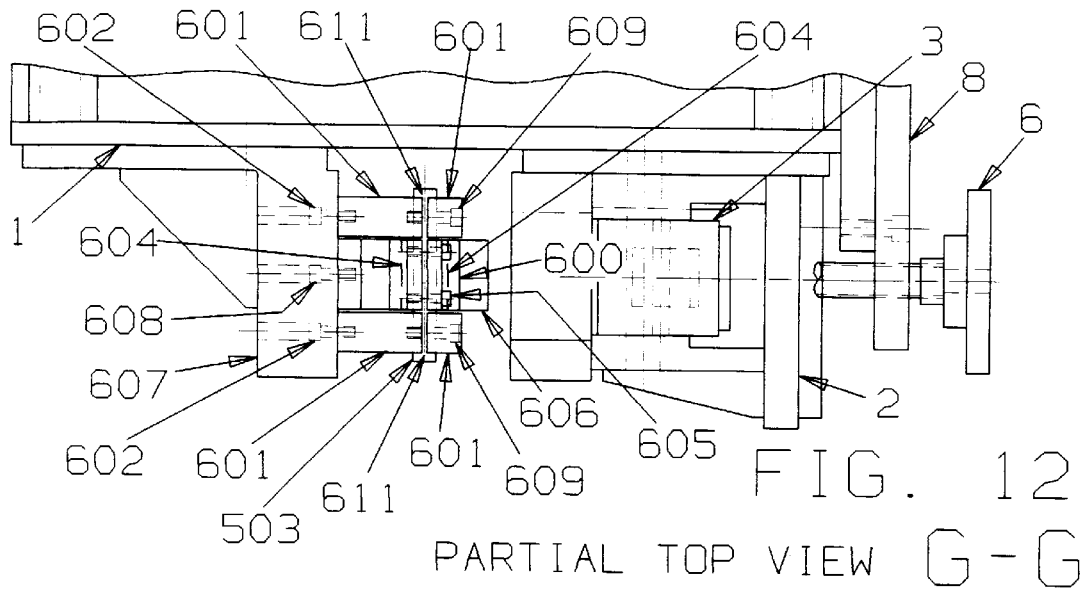

SECTION H-H

MECHANICAL STRESS TEST MACHINE

This application claims the benefit of U.S. Provisional application No. 60/031,146, filed Nov. 19, 1996.

FIELD OF THE INVENTION

The invention relates generally to apparatuses for testing of materials subject to bending, tensile, compressing, and/or torsioning loads.

BACKGROUND OF THE INVENTION

A type of machine for providing cyclic or non-cyclic stresses to a material presently exists of a nature such that very expensive servo controlled hydraulics are employed to control force, stroke, and cycle rate. While these machines are capable of operating over a wide range of speeds, the disadvantages are high initial cost for both hardware and software, as well as high filtration requirements of the hydraulic system to prevent contamination and damage to any of the sophisticated hydraulic components. Maintenance of these machines are costly and is usually performed by a specialist in hydraulics and other specialists for solving computer hardware and software problems.

Another type of machine in use in this field is electrically controlled sliding members, often driven by a rotating screw. While this is lower in cost than the first example, it is not nearly as capable of high cyclic rates and loads.

Machines for providing stresses to material have also been described in the patent literature. For example U.S. Pat. No. 5,421,205 "Apparatus for the rapid ultimate material strength testing" of A. Pohl, U.S. Pat. No. 3,733,895 high speed fatigue tester by Ishida, and U.S. Pat. No. 3,808,885, a Spring tester by Carlson, incorporated herein by reference, are presented for the background of the reader.

These and other approaches do not offer the same advantages as the present invention. In particular there is a need for cost effective devices, devices which are simple to operate, which are minimal upkeep and which can be easily adapted to a variety of test conditions and part configurations.

SUMMARY OF THE INVENTION

The invention relates generally to an apparatus for testing materials by subjecting the materials to any combination of bending, tensile, compressive, or torsional loads, either fixed or moving relative to the test specimen, depending upon the test being performed.

The loads may be cyclic in order to determine the number of cycles to failure of the material being tested. These loads may be applied at any required cyclic rate, and up to any number of cycles required.

In addition a load may be applied once in excess of the strength of the material being tested in order to determine it's yield point or ultimate strength.

It is an object of the present invention to provide a useful machine for mechanical stress testing of materials.

A further object is to provide adjustable load and speed for providing periodic stresses.

A further object is to have a machine with readily interchangeable fixtures for testing different shaped parts.

A still further object is to have a machine with changeable set-ups and test conditions.

A further object of the invention is to provide a machine which tests valve stems.

These and other objects of the present invention will become more readily appreciated and understood from a consideration of the following detailed description of the preferred embodiments when taken together with the accompanying drawings.

BRIEF DESCRIPTION OF THE DRAWINGS

FIG. 4 is a partial sectional view of . . . at A—A showing a cam shaft and test specimen.

FIG. 5 is partial sectional view of . . . at C—C through left hand lever.

FIG. 11 is a partial front view of a cyclic torsion setup.

FIG. 12 is a partial top view at G—G of the cyclic torsion setup of FIG. 11.

DETAILED DESCRIPTION OF THE PREFERRED EMBODIMENT

Figure 1:
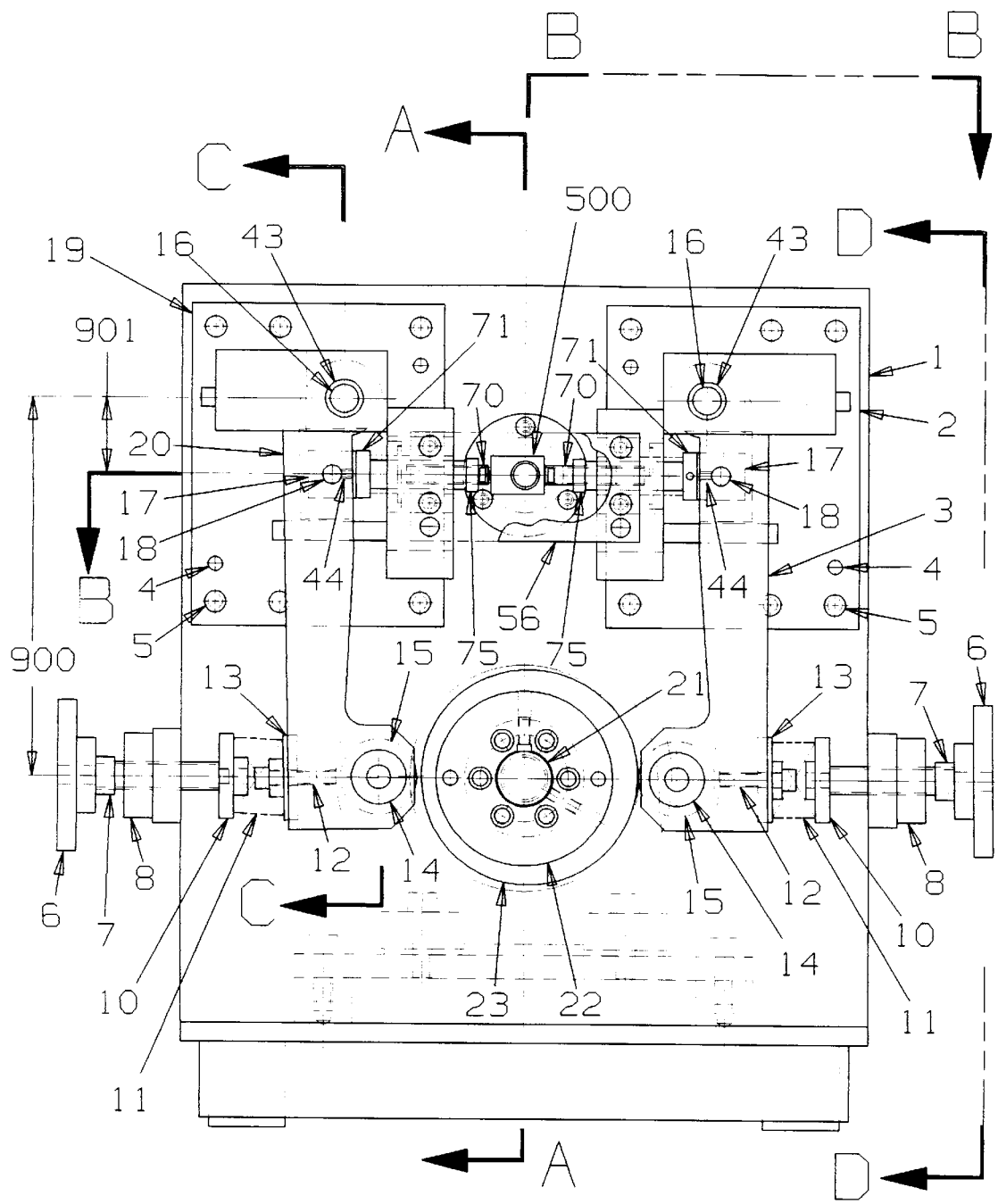
FIG. 1 is a front view of a cyclic alternating side load setup.
Figure 2:
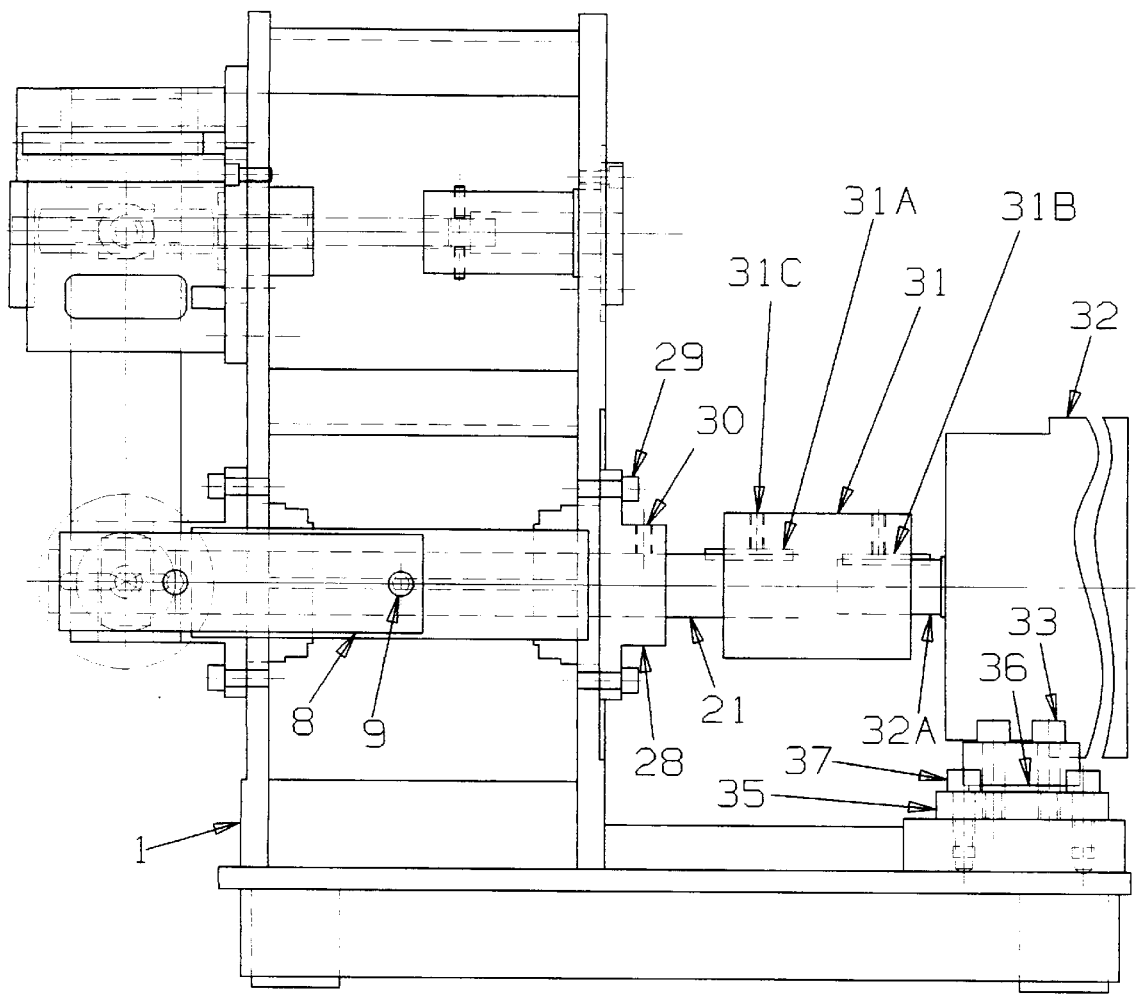
FIG. 2 is a right side view of the setup of FIG. 1 at D—D.

This machine as shown in FIG. 1 and FIG. 2 is comprised of a machine frame 1, having a, rotating camshaft or eccentric 21, a prime mover (such as an electric motor) 32, and lever arms 3 and 20 which pivot around pivot points 16 to transfer cyclic forces to sample specimen 500.

This machine is not limited to any particular cam or eccentric, or linkage, but may use-any means to provide a primary external force. In FIG. 1 this force is shown being applied by, but not limited to, a compression spring 11. Any suitable force applicator will be offered to replace or work in conjunction with the spring 11. For instance a pneumatic, hydraulic, or electric type primary force applicator is an optional part of this machine and will be furnished as ordered by the purchaser.

FIG. 1 shows a front view of the machine as set up for a cyclic side load test. The rotation of cam 23 which is in contact with lever camroll 15, causes oscillation of right hand lever 3 and left hand lever 20 by overcoming the force of springs 11. This lever oscillation causes a cyclic loading and unloading of test specimen 500.

The force is transmitted from compression spring 11 through effort arm 900 (the distance at right angles between the center of pivot 16 to the center of the force applied by spring 11) to resistance arm 901 (the distance at right angles from the center of pivot 16 to the center of motion of slide 71. This force ultimately is transmitted to test specimen 500.

Looking at FIG. 1 the right hand lever bracket 2, and the left hand lever bracket 19, are fastened to the machine frame 1 with cap screws 5, and dowel pins 4 fix a precise repeatable location when machine re-assembly is required. Optional wear bushings 43 are shown pressed into pivot holes in brackets 2 and 19. See FIG. 5 which shows the pivot shafts 16 assembled through two pivot holes in brackets 2 and 19 as well as through pivot hole in right hand lever 3, and left hand lever 20. The two pivot shafts 16 are retained by retaining screw 42 in pivot levers 3 and 20.

Optional lubrication fittings 41 are assembled in lever brackets 2 and 19 and provide a means to lubricate pivot shafts 16. The thrust bearings 41A serve as side wear surfaces side wear surfaces while maintaining the proper axial location of levers 3 and 20.

The lever cam roller 15 which is at the lower end of levers 3 and 20 is assembled on cam roll shaft 14 which is held in place on levers 3 and 20 by lock washer 47, washer 48 and hex nut 46.

In FIG. 1 cam rollers 15 are shown for purposes of illustration at the lower end of each lever 3 and 20. These cam rollers being in contact with cam or eccentric 23 are thrust outward from cam center of rotation during cam rise, causing levers to pivot outward about pivot shafts 16 and the external force from spring is transferred from the test specimen 500, which is at this point free from the external testing load, because the external force has been transferred to the cam 23.

The cam rollers 15 are held in contact with the cam 23 by the force imparted by springs 11 which push on wear discs 13. The wear discs 13 are held onto levers 3 and 20 by cap screws 12. The outer wear disc 10 is held in place by a pilot diameter on the nose end of the adjustable stud assembly 6. A stud stop tube 7 slips over the adjustable stud assembly 6 outer diameter to limit spring load adjustment thus preventing overloading of machine components or the test specimen 500.

The adjustable stud assembly 6 is threaded through plate 8 which is held in place by cap screw 9 (see FIG. 6) and is adjusted to obtain the desired force on the test specimen 500. This force can be measured by any acceptable method desired by the user, and may be attached as optional equipment.

Figure 3:
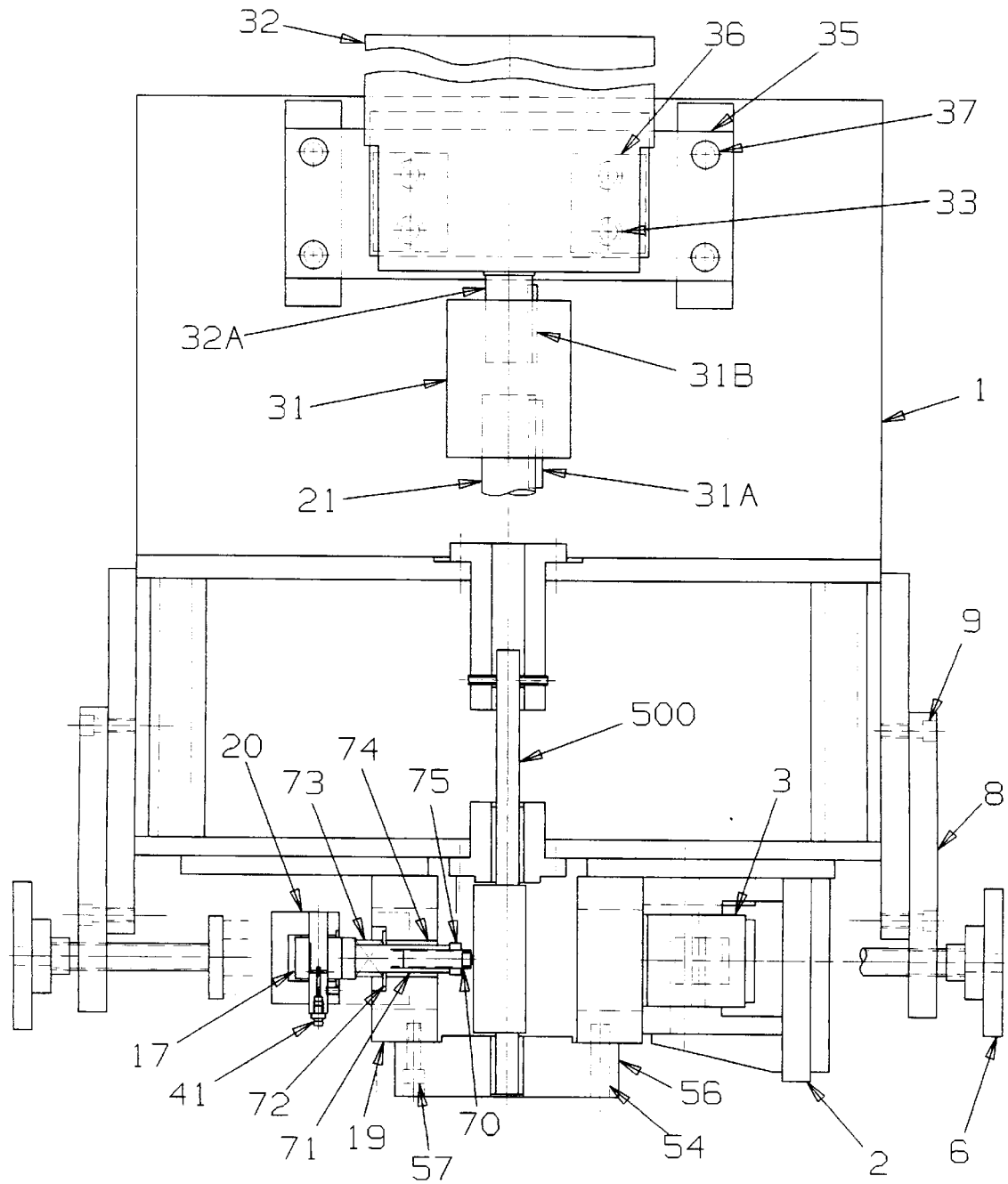
FIG. 3 is a partial sectional view of the setup of FIG. 1 at B—B.

FIG. 2 which is a sectional view D—D of FIG. 1 and FIG. 3 which is a sectional view B—B of FIG. 1 show mounted bearing units 28 are held onto frame 1 by cap screws 29. Two bearing units 28 are shown in FIG. 2 in this particular configuration. Set screws 30 are but one means to lock the inner race of bearing unit 28, to camshaft 21.

A prime mover mount 35 is attached to machine frame 1 by cap screws 37. Spacers 36 to align prime mover output shaft 32A with camshaft 21 and are assembled between prime mover 32 and prime mover mount 35 and held in place by cap screws 33.

A coupling 31 is assembled between output shaft of prime mover 32A (such as a motor) and camshaft 21. Keys 31A and 31B provide for a positive drive through coupling 31 to camshaft 21 and output shaft of prime mover 32A. The coupling 31 is held axially in place by set screws 31C.

One example of a cam mounting method is shown in FIG. 4 which is sectional view A—A of FIG. 1. A cam hub 22 is assembled near the front of the camshaft 21, and over a positive drive key 52. The cam hub 22 is retained axially onto camshaft 21 by set screw 51. A cam or eccentric 23 of any suitable shape is assembled on the cam hub 22, and locked between cam hub 22 and clamping disc 50 by means of cap screws 53. The friction between both sides of cam 23 with the friction surfaces 22A of cam hub 22, and clamping disc 50 keep the cam from slipping radially when machine is in operation, yet, when required during machine setup, the cam 23 can easily be adjusted radially by loosening cap screws 53 and re-tightening once the proper setting is obtained.

The following are two examples of many force measurements that could be used on this machine, but the machine is by no means limited to these.

The first example uses simply a compressed length of spring 11, with a known spring rate. The length can be measured to determine the external force, since force is proportional to the amount of compression. The spring rate is a change in load per unit of deflection.

A second example, and more precise method, uses a load cell, a transducer which converts a load acting on it into an electrical signal which can be read on an output device, such as a digital readout. The transducer can be set up to reflect either the load on the test specimen 500, or on the test specimen bushings 55 and 59 shown in FIG. 4, or on any suitable points in the system, and calibrated accordingly.

The pivot blocks 17 as seen in FIGS. 1, 3 and 5 (a sectional view C—C of FIG. 1) are assembled into right hand lever 3 and left hand lever 20 and retained by pivot block shafts 18 which are assembled through levers 3 and 20 as well as thrust bearings 45 (see FIG. 5) which locate pivot blocks axially and also serve as side wear surfaces. The pivot block shaft is held in place by a set screw 44. An optional lubrication fitting 41 is shown threaded into the end of pivot block shaft 18 and carries lubrication through the pivot block shaft 18 to lubricate the inside diameter of the pivot blocks 17.

FIG. 3 shows a top view of slide 71 held in contact with pivot block 17 by spring 73 which also bears against fixed thrust bearings 72, thus any motion of pivot block 17 causes a relative motion of slide 71. Slide 71 in this case is contained by wear bushing 74, which is pressed into lever brackets 2 and 19. A threaded stud 70, is adjusted to contact and transmit the required load to test specimen 500. A locknut 75 prevents unwanted rotation of stud 70 by locking it to slide 71.

This machine is capable of testing a wide variety of sizes and shapes of test specimens. Only one example is given for each cyclic bending, cyclic compressive, cyclic tensile, and cyclic torsion tests in the interest of brevity.

As an example of the test specimen 500 being located and retained for a typical cyclic bending test see FIG. 4. With the outer support 56 removed, the test specimen 500 is inserted through the bushings 59 and 61. The bushing 59 is pressed into the adapter 60 which is attached to the front face of the machine frame 1 by means of cap screws 58. The bushing 61 is pressed into the adapter 64, which is attached to the rear face of the machine frame 1 by means of the cap screws 63. The set screws 62 are but one means to hold test specimen 500 in place.

The outer support 56 is then assembled over the outer end of the test specimen 500 and over locating pins 54 and held in place by the cap screws 57. The bushing 55 is pressed into the outer support 56, and slips over and supports the outer end of the test specimen 500, which is now in position for a cyclic bending test. In this example the part is supported on both sides of the load, which is applied by the threaded stud 70.

Figure 6:
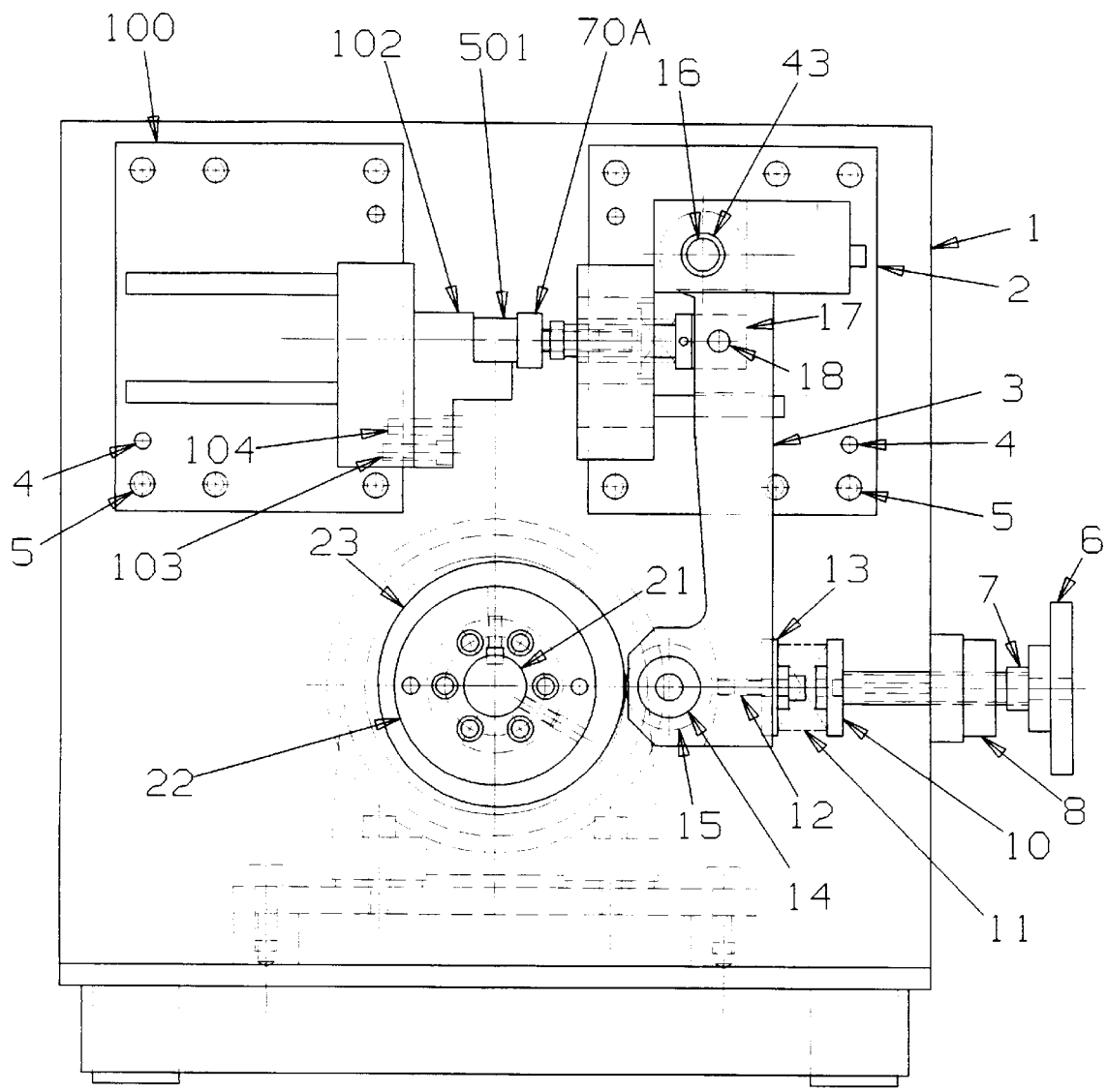
FIG. 6 is a front view of a cyclic compressive setup of the present invention.

FIG. 6 is a front view of the machine showing the machine setup for a cyclic compressive test. The fixed bracket 100 has taken the place of left hand lever bracket 19 and all its assembled components.

The compression test fixture 102 is mounted to bracket 100 by cap screws 103 and dowels 104, and will contain all the necessary components to locate and retain the test specimen 501 in a fixed position for cyclic compression testing.

Rotation of camshaft 21, causes oscillation of the machine components that are a part of the right hand mounting bracket assembly as previously described for the alternating cyclic side load setup, but in this setup the test specimen 501 is under a cyclic compressive load which is applied by compressive load member 70A.

Figure 8:
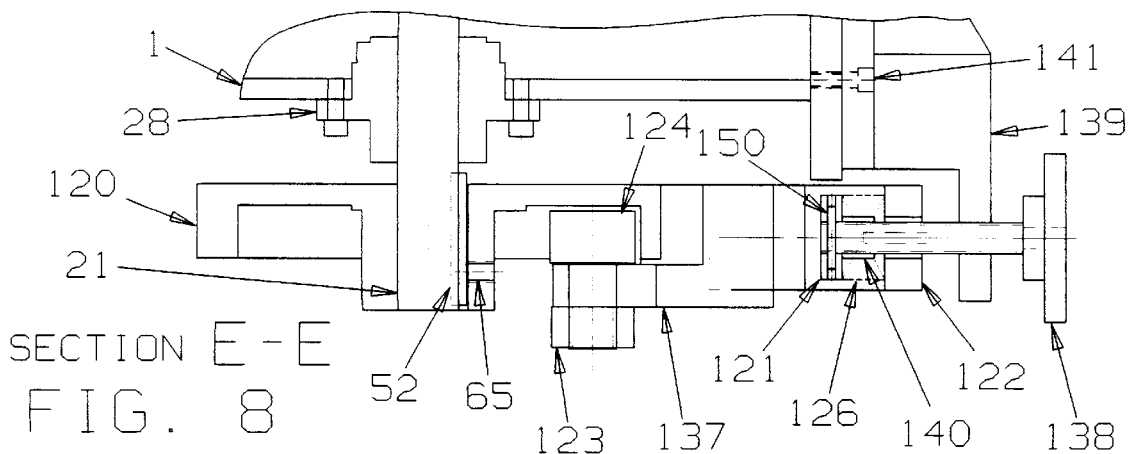
FIG. 8 is a partial sectional view at E—E of FIG. 7 through the cam shaft.
Figure 7:
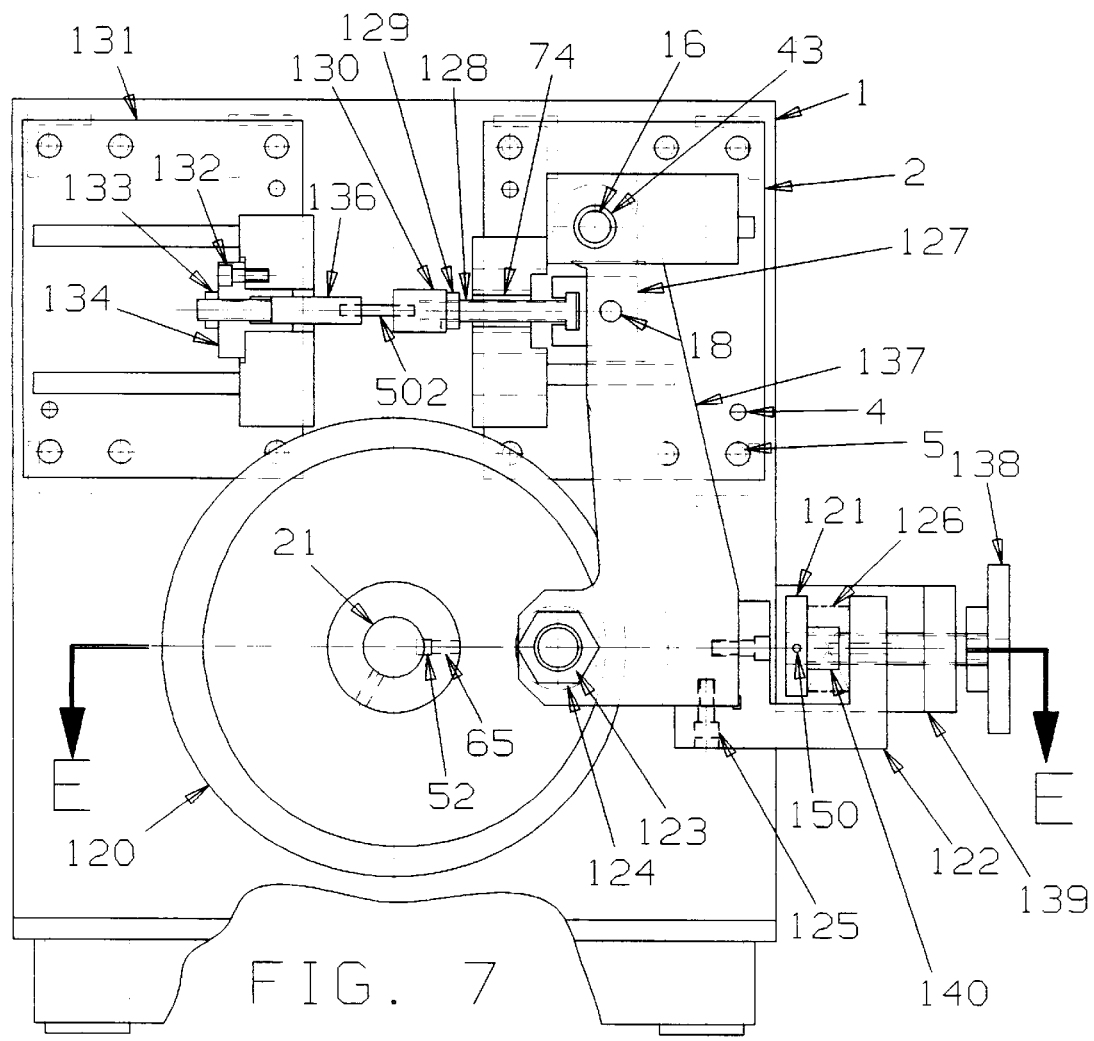
FIG. 7 is a front view of a cyclic tensile setup of the present invention.

FIGS. 7 and 8 show the machine setup for a cyclic tensile test. In FIG. 7 the fixed bracket 131 is shown mounted in the left hand position, and holds a gripper assembly 136 for gripping and retaining the tensile test specimen 502. For example, a gripper assembly 136 of any type commonly used to grip test specimens, is piloted and threaded into an adapter bushing 134 and locked in position by lock-nut 133. The adapter bushing 134 is retained by cap screws 132.

The right hand mounting bracket assembly consists of, and operates like the prior setups for cyclic bending or compression, except for the tooling changes required to impart a tensile load to the test specimen.

An example of a gripper unit 130 of any common type to grip the right end of test specimen 502 is seen in FIG. 7. This gripper unit 130 is retained in position by a tee bolt 128, and locked in position by locknut 129. The tee bolt 128 slides in bushing 74 which is pressed into the right hand bracket 2. The head of the tee bolt 128 is captive in the tee slot in the pivoting block 127 which pivots about pivot block shaft 18.

A stud type cam follower 124 is mounted on the right hand lever 137 and retained by nut 123. The cam follower 124 engages a rotating closed track cam 120 in this case shown engaged in such a manner that as the cam curve moves closer to the center of rotation, the right hand lever 137 pivots about pivot shaft 16, and is pulled clockwise toward the camshaft, thus releasing the tensile load on the test specimen 502. The closed track cam 120 is mounted to camshaft 21 and is positively driven by key 52 and is retained to camshaft 21 by set screw 65.

A spring adapter 122 is mounted to the end of lever 137 and held in place by cap screws 125. A spring retainer 121 is threaded to end of the adjustable stud assembly 138 and pinned in place by dowel 150. The compression spring 126 is contained between spring retainer 121 and the spring adapter 122. The outer end of the adjustable stud assembly 138 is threaded into the bracket 139 which is fixed to frame 1 by cap screws 141. The stud stop tube 140 limits the spring load adjustment.

As the closed track cam 120 rotates and the cam curve increases toward a larger radius, the force from compression spring 126 causes a counter-clockwise rotation of tensile test lever 137. When the force of the spring is balanced by the opposing force caused by the strain in the test specimen 502, movement of the tensile test lever 137 ceases. The cam continues to rotate to a still larger radius, causing the stud type cam follower 124 to become disengaged from the cam curve, thus insuring that all the spring force is transmitted to the test specimen 502, which is now under tension.

As the cam 120 continues to rotate and the cam curve reverses to a decreasing radius, at some point the cam curve re-engages the stud type cam follower 124 and overcomes the force of spring 126. This causes the lever 137 to move clockwise and removes the tensile force which has been induced in the test specimen 502.

FIG. 8 is a partial section at E—E of FIG. 7 through cam shaft. A stud type cam follower 124 is mounted on the right hand lever 137 and retained by nut 123. The cam follower 124 engages a rotating cam 120 in this case shown engaged in such a manner that as the cam curve moves closer to the center of rotation, the lever 137 is pulled clockwise toward the camshaft, thus releasing the tensile load on the test specimen.

A spring adapter 122 is mounted to the end of lever 137 and held in place by cap screws 125. A spring retainer 121 is threaded to end of the adjustable stud assembly 6 and pinned in place by dowel 150. The compression spring 126 is contained between spring retainer 121 and the spring adapter 122. The outer end of the adjustable stud assembly is threaded into the plate 8, which is a fixed member as shown in previous examples.

As the cam 120 rotates and the cam curve increases toward a larger radius, the force from spring 126 causes a counter-clockwise rotation of lever 137. The cam continues to rotate to a still larger radius, causing the stud type cam follower 124 to become disengaged from the cam curve, thus insuring that all the spring force is transmitted to the test specimen 502 which is now under tension.

As the cam 120 continues to rotate and the cam curve reverses to a decreasing radius, at some point the cam curve re-engages the stud type cam follower 124 and overcomes the force of spring 126. This causes the lever 137 to move clockwise and removes the tensile force which has been induced in the test specimen 502.

Figure 10:
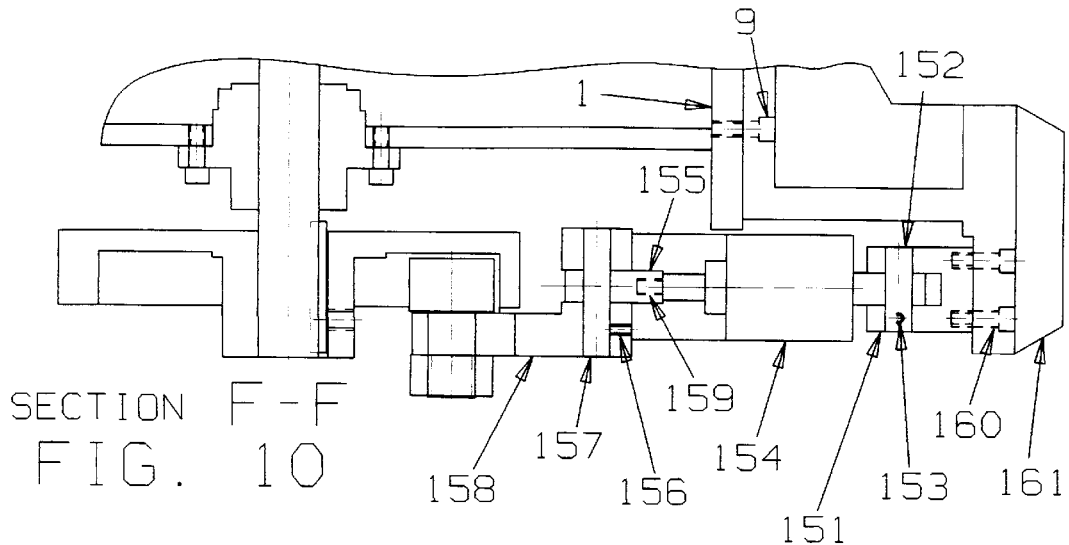
FIG. 10 is a partial sectional view at F—F of the setup of FIG. 9.
Figure 9:
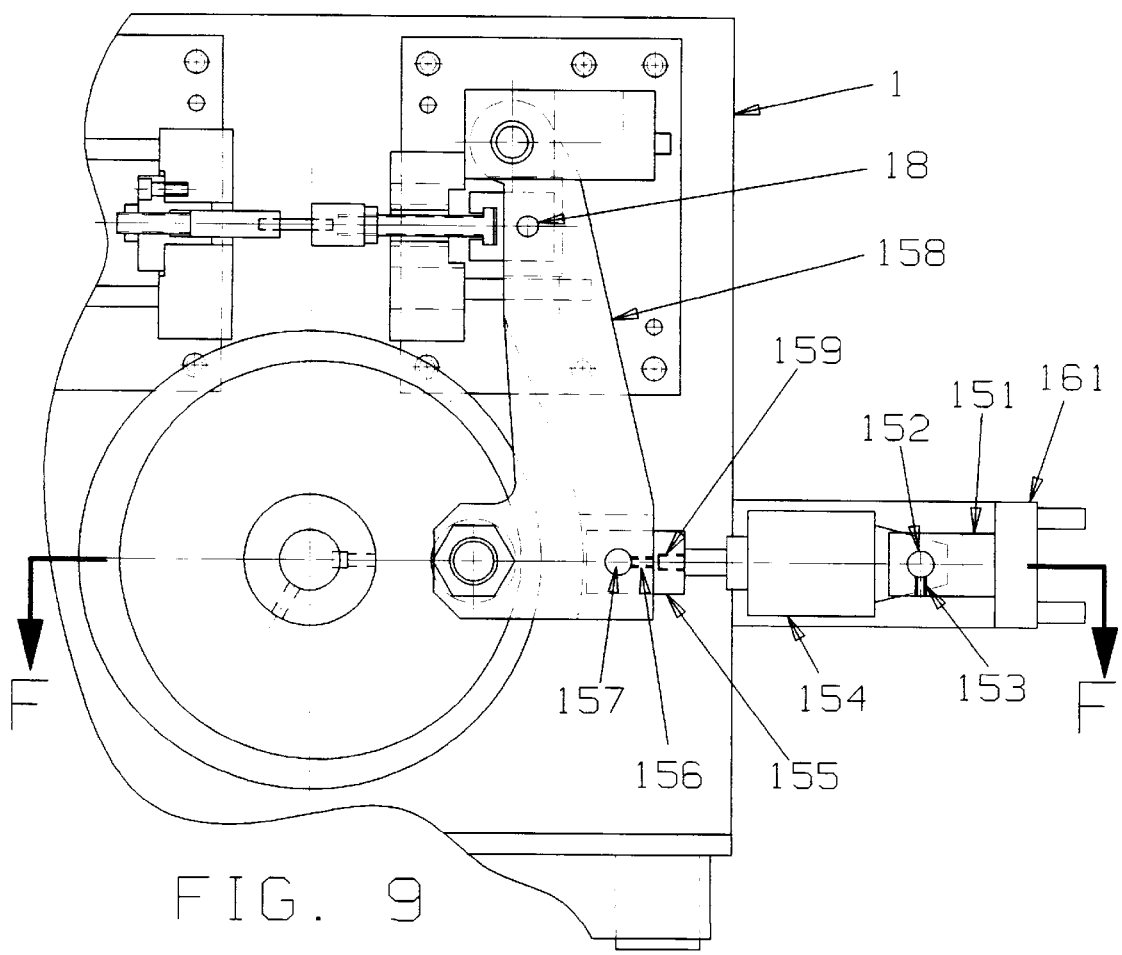
FIG. 9 is a front view of a cyclic tensile setup with hydraulic or pneumatic cylinder option to provide the external force.

FIGS. 9 and 10 show a cyclic tensile setup with hydraulic or pneumatic cylinder option as primary force applicator (the external force). FIG. 9 is a front partial view. A cylinder mounting bracket 161 is mounted to the right side of the frame 1 using cap screws 9. Yoke 151 is attached to the cylinder mounting bracket 161 by cap screws 160. A pivot pin 152 is inserted into holes in the yoke 151 and the rear pivot hole of the cylinder 154 and is retained by set screw 153. The cylinder rod end 159 is screwed into knuckle 155. The pivot pin 157 attaches the knuckle 155 to the right hand lever 158 and is retained by set screw 156. The remaining parts in this setup are the same as shown in FIGS. 7 and 8.

FIG. 10 is a partial sectional view et F—F of FIG. 9. Of particular interest is the manner in which a pneumatic or hydraulic cylinder 154 is connected to the lever arm 158 by means of cylinder rod end 159 being screwed into knuckle 155. The pivot pin 157 attaches the knuckle 155 to the right hand lever 158 and is retained by set screw 156. On the other end the cylinder 154 is connected to yoke 151 which in turn is attached to the cylinder mounting bracket 161 by cap screws 160. A pivot pin 152 is inserted into holes in the yoke 151 and the rear pivot hole of the cylinder 154 and is retained by set screw 153.

FIGS. 11 and 12 show a cyclic torsion setup. In FIG. 11 is a partial front view of a cyclic torsion setup. FIG. 12 is a partial top view at section G—G of the cyclic torsion setup illustrated in FIG. 11.

In FIG. 11 the rotating cam 23 imparts motion to the right hand lever 3 and all its related parts. The torsion bracket 607 is shown mounted in the left hand position on frame 1 and provides a means to mount parts necessary to conduct any variety of torsional tests.

This particular setup shows a torsion test specimen 503, having a cylindrical shape, being held on each end of its outside diameter by the torsion retainers 601 which have a torsion retainer sawcut 611 and a torsion retainer clamp screw 609 to hold the torsion test specimen 503 against slipping both radially and axially in the torsion retainers 601. The torsion retainers 601 are assembled to the torsion bracket 607 and held in place by cap screw 602 and dowel pin 603.

The torsion arm 600 is clamped onto the center portion of torsion test specimen 503 and between torsion retainers 601. The torsion arm 600 is clamped to the torsion test specimen 503 by torsion arm clamp screws 605 which squeeze through the torsion arm sawcut 610 to clamp on the outside diameter of the torsion test specimen 503.

A torsion arm bearing support 606 is assembled to the torsion bracket 607 and held in place by cap screws 608. The torsion arm bearings 604 are provided to eliminate bending of torsion test specimen 503 by counteracting the horizontal force applied by threaded stud 70.

The force for this torsion test is applied by the threaded stud 70 to the torsion arm 600 at a suitable radial distance from the center of the torsion test specimen 503.

The amount of force and its frequency and source is the same as previously described.

Figure 14:
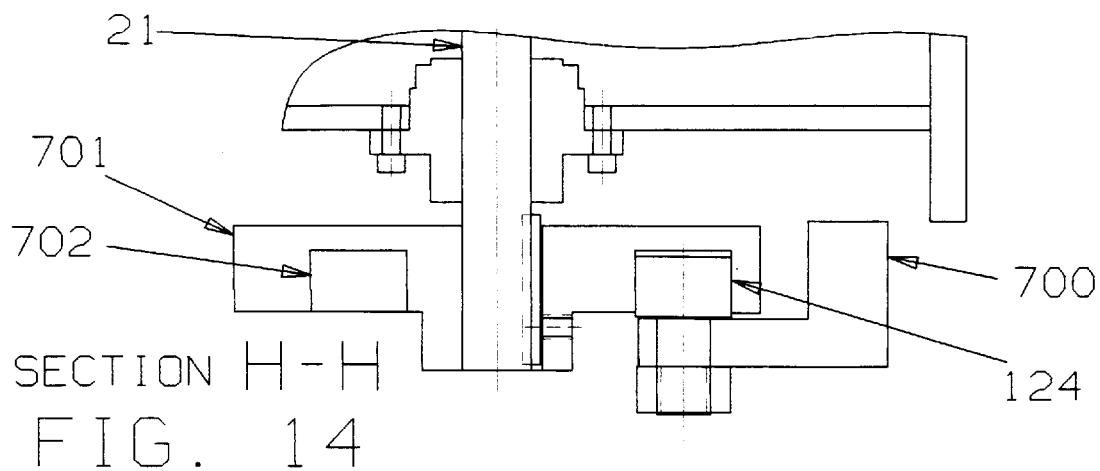
FIG. 14 is a partial sectional view of H—H through FIG. 13.
Figure 13:
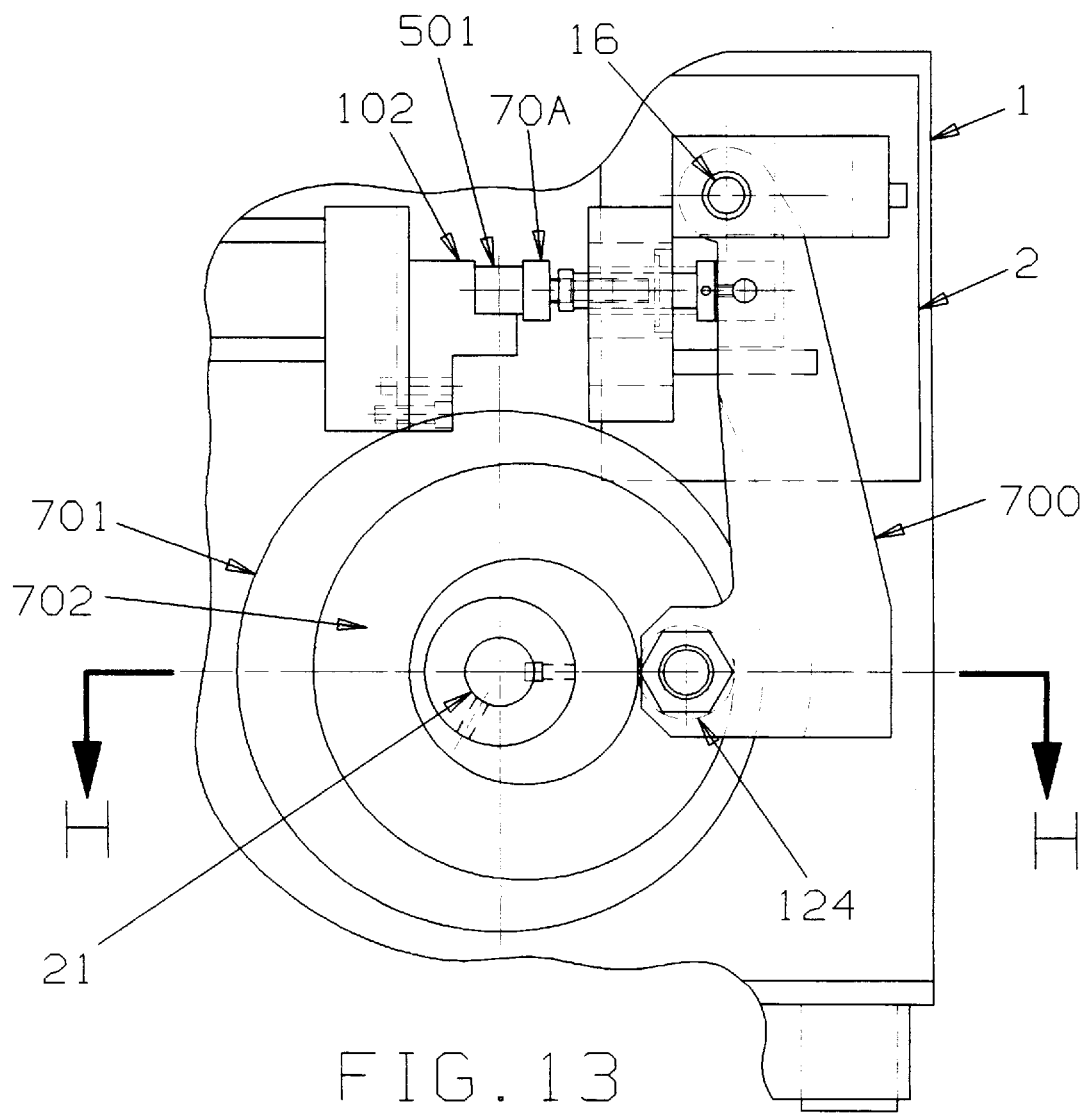
FIG. 13 is a partial front view of a control of cam angular position.

FIG. 13 is a partial front view illustrating cam angular position control. FIG. 14 is a partial top view at section H—H of FIG. 13 further illustrating the inside cam 701. FIGS. 13 and 14 show a setup where the precise control of the angular position of the camshaft 21 by any well known method including but not limited to servo and stepping motors will determine the deflection or load at the test specimen 501.

A compressive stress test is shown in this example, however any type of stress test using this camshaft angular position method, can be conducted simply by using the machine components and tooling required to conduct the desired test.

By controlling the angular position of the camshaft 21, the closed camtrack 702 in cam 701, controls the displacement of the stud type cam follower 124, which causes the right hand lever to pivot about pivot shaft 16. This moves all related moving machine members as described previously. This allows the loading member 70A to move to any position required to obtain the desired deflection or load on the test specimen 501.

Figure 15:
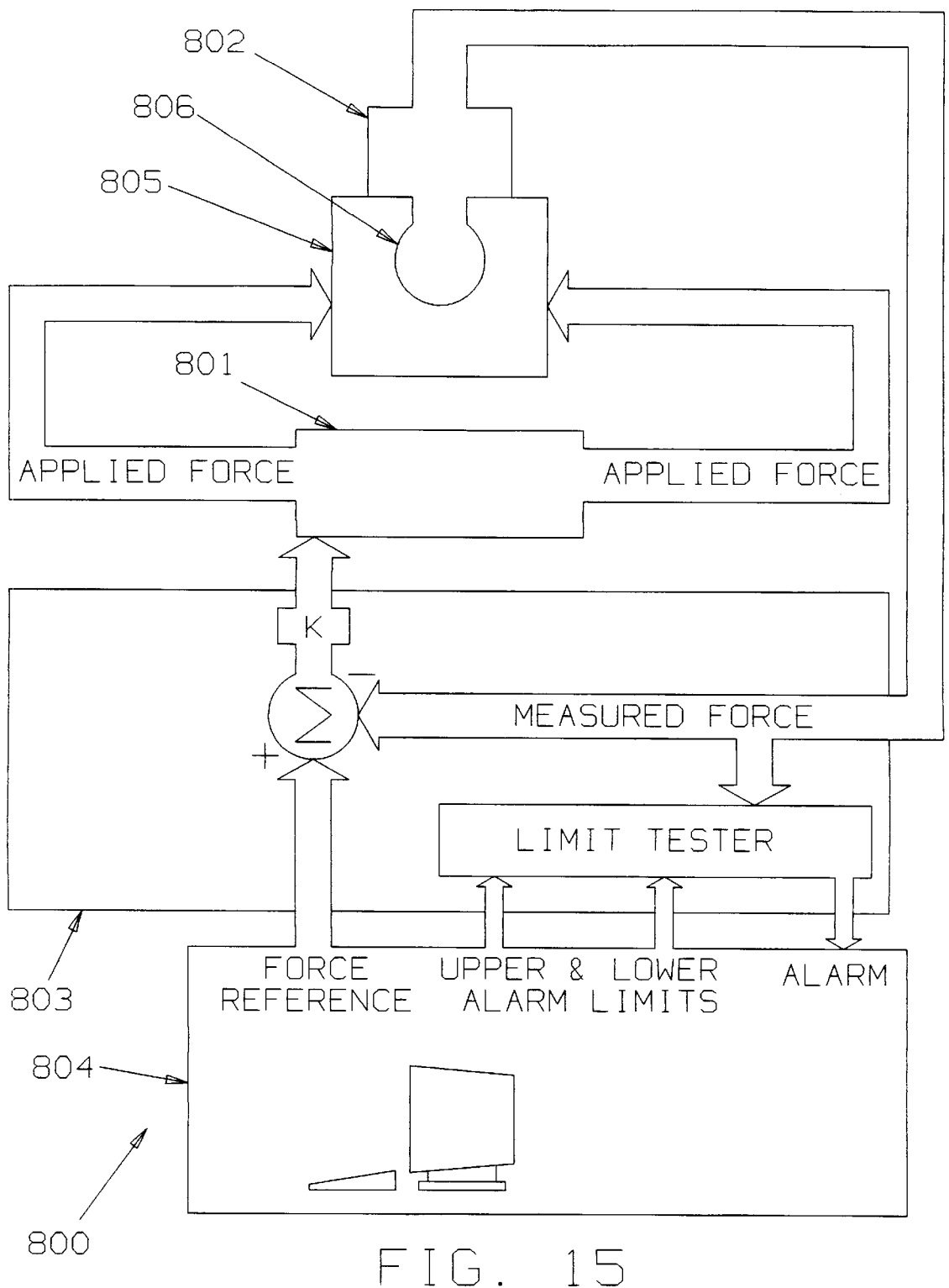
FIG. 15 is a control schematic of an electronically regulated force application system.

FIG. 15 is a control schematic of an electronically regulated force application system 800. The system 800 consists of four distinct sub-systems; a force actuation unit, 801; a load cell, 802; a force regulator, 803 and an input control panel, 804. The primary objective of this system is to provide for a precisely controlled force to be applied to the unit under test (UUT), 806, under all operating conditions and time. Secondary objectives include, but are not limited to, ease of force set up and operator alarm upon UUT failure.

The purpose of the force actuation unit 801, is to provide a means to supply the primary force to the machine 800 which ultimately gets transferred to the UUT, 806. The input to this system is either an electrical analog or digital control signal and the output is a force proportional to the control input signal. This system could be realized by, but not limited to, a pneumatic, hydraulic or spring and servo-motor control scheme.

The load cell, 802 is used to measure the force being applied to the UUT 806. The input to this system is a force and the output is an electrical analog or digital control signal proportional to the applied force.

The force regulator 803 is an electrical control circuit which is responsible for ensuring the desired force is applied to the UUT 806. The inputs to this system are the output from the load cell and an analog or digital control signal which is proportional to the force that the operator would like to be applied to the UUT 806. One output from this system is a digital or analog control signal which is connected to the force actuation unit input 801 and provides the appropriate input to maintain a constant force for the UUT 806. Another output from this system could be an alarm signal used to alert the operator if the output from the load cell 802 is out of a specified range, indicating a possible failure of the UUT 806.

The input control panel 804 is the means by which the operator can input the force to be applied to the UUT 806. The input device could be, but is not limited to, a numeric keypad with a local liquid crystal display (LCD) or light emitting diode (LED) display or a personal computer. One output from this system is an analog or digital control signal which is sent to the force regulator 803. This signal is proportional to the force which is to be applied to the UUT 806. A second output from this system could be limits to which the output from the load cell 802 are measured against in the force regulator 803. These signals are analog or digital signals which represent minimum and maximum limits for the load cell output. An input to this system could be an alarm signal from the force regulator 803 indicating the force being applied to the UUT 806 is outside specified limits. This signal would sound an audible alarm or perhaps halt the machine.

We claim:

1. A stress test machine comprising:
   a lever having an effort arm, a resistance arm and a fulcrum;
   a cam applying a cyclicly varying first force to the effort arm of said lever;
   a load source applying a second force to the effort arm of said lever, wherein said first force opposes said second force; and
   a sample holder located adjacent to the resistance arm of said lever, such that when a test sample is placed in said holder force applied to said effort arm is transferred to said test sample.

2. The machine of claim 1 further wherein said load source is adjustable.

3. The machine of claim 1 further comprising:
   means for measuring said load force.

4. The machine of claim 1 wherein said force is transferred compressively to said test sample.

5. The machine of claim 1 wherein said force is transferred extensively.

6. The machine of claim 1 wherein said load force is applied hydraulically.

7. The machine of claim 1 wherein said load force is applied pneumatically.

8. The machine of claim 1 wherein said load source further comprises a spring.

9. The machine of claim 1 wherein said load source further comprises a servo motor.

10. The machine of claim 1 wherein said load force is transferred torsionally.

11. The machine as of claim 1 further comprising a force regulator.

12. The machine of claim 11 further comprising a display.

13. The machine of claim 11 further comprising a keypad and actuator.

14. The machine of claim 1 further comprising a means for reducing off axis transfer of force.

15. A stress test machine comprising:
- a lever having an effort arm, a resistance arm and a fulcrum;
- a cam applying a cyclicly varying first force to the effort arm of said lever;
- means for angular positioning of said cam for adjusting said first force; and
- a sample holder located adjacent to the resistance arm of said lever, such that when a test sample is placed in said holder, force applied to said effort arm is transferred to said test sample.

16. The machine of claim 15 further comprising a means for stepping said cam.

17. The machine of claim 16 wherein said means for stepping said cam is a stepper motor.

18. The machine of claim 1 wherein said cam further comprises a multiplicity of high spots.

19. The machine of claim 1 further comprising means for periodically reversing the motion of said cam.

20. The machine of claim 1 wherein force multiplication of said load force is variable between −100 and +100.

* * * * *